United States Patent [19]
Johnson

[11] Patent Number: 5,183,937
[45] Date of Patent: Feb. 2, 1993

[54] ACETIC ACID RECOVERY

[75] Inventor: Mark R. Johnson, Grayslake, Ill.

[73] Assignee: The NutraSweet Company, Deerfield, Ill.

[21] Appl. No.: 798,361

[22] Filed: Nov. 21, 1991

Related U.S. Application Data

[63] Continuation of Ser. No. 479,902, Feb. 7, 1990, abandoned.

[51] Int. Cl.$^5$ ............................................... C07B 51/42
[52] U.S. Cl. .................................................... 562/608
[58] Field of Search ......................................... 562/608

[56] References Cited

U.S. PATENT DOCUMENTS

| | | | |
|---|---|---|---|
| 3,933,781 | 1/1976 | Bachman et al. | 260/112.5 |
| 4,526,985 | 7/1985 | Giobbio et al. | 549/253 |
| 4,550,180 | 10/1985 | Takemoto et al. | 549/253 |
| 4,810,816 | 3/1989 | Tsuji et al. | 560/41 |

FOREIGN PATENT DOCUMENTS 531751 10/1956 Canada .................................. 562/608

*Primary Examiner*—Arthur C. Prescott
*Attorney, Agent, or Firm*—Jeffrey M. Hoster

[57] ABSTRACT

A process for recovering acetic acid from a mother liquor containing acetic acid, formic acid, acetic anhydride and formic acetic anhydride comprising the steps of:

(a) heating said mother liquor to a temperature greater than or equal to about 70° C. for a time period ranging from about 1 hour to about 24 hours to convert all of said formic acetic anhydride to acetic acid and gaseous carbon monoxide and to fully deplete either said acetic anhydride or said formic acid, whichever is initially present in a stoichiometric lesser amount and thereby produce a mixture comprising acetic acid and either acetic anhydride or formic acid, whichever has been depleted; and (b) separating said acetic acid from the remainder of said mixture produced in step (a) is provided.

7 Claims, No Drawings

ACETIC ACID RECOVERY

This is a continuation of co-pending U.S. application Ser. No. 07/479,902, filed Feb. 7, 1990, now abandoned.

BACKGROUND OF THE INVENTION

1. Field of the Invention

The present invention relates to a process for recovering acetic acid from a mother liquor, and more particularly, to a process for recovering acetic acid from the mother liquor used in the formation of N-formylaspartic anhydride.

2. Description of the Prior Art

Aspartame, α-L-aspartyl-L-phenylalanine methyl ester, is a sweetening agent which is approximately 100–200 times sweeter than sucrose. As a result, aspartame has been widely used as a substitute for sucrose in beverages, foods, and the like.

A number of methods have been proposed for synthesizing aspartame. One such method comprises reacting N-protected aspartic acid anhydride with L-phenylalanine or its methyl ester, typically in an acetic acid solvent, followed by esterification of the reaction product. This method is described in greater detail in U.S. Pat. Nos. 3,933,871 and 4,810,816. As noted above, the starting material used for the aspartame synthesis comprises an N-protected aspartic acid anhydride, and particularly N-formylaspartic anhydride. The anhydride is typically prepared by reacting amounts of aspartic acid, formic acid and acetic anhydride. This reaction optionally takes place in the presence of co-solvents or metal catalysts. Methods for producing N-formylaspartic anhydride are disclosed in greater detail in U.S. Pat. Nos. 3,933,871; 4,526,985; 4,550,180; and 4,810,816.

The resultant mixture produced by the synthesis of N-formylaspartic anhydride comprises N-formylaspartic anhydride crystals in a mother liquor. In practice, the crystals may be separated from the mother liquor prior to reaction with the L-phenylalanine (or its methyl ester) or the L-phenylalanine may be directly added into the crystals/liquor mixture. The former method is particularly advantageous as it enables higher yields of aspartame to ultimately be obtained and results in a more pure final product as the impurities which are present in the mother liquor are not transferred to the crystals.

The mother liquor remaining after separation of the crystals comprises acetic acid, acetic anhydride, formic acid, formic acetic anhydride and high boiling components derived from aspartic acid, with acetic acid being present in the most predominant amount. Due to the value of acetic acid, it is desirable to recover it in relatively pure form from the mother liquor. One method for doing this comprises separating the aspartic acid derived components from the remainder of the mother liquor and using a four component fractional distillation to isolate the acetic acid. This process is problematical as it is extremely expensive and tedious.

Accordingly, there exists a need in the art for a simplified process for recovering acetic acid from a mother liquor including acetic acid, formic acid, acetic anhydride and formic acetic anhydride.

SUMMARY OF THE INVENTION

In accordance with the present invention, a simplified process for recovering acetic acid from a mother liquor including acetic acid, formic acid, acetic anhydride and formic acetic anhydride is provided. In a preferred embodiment, the process comprises the steps of:

(a) heating said mother liquor to a temperature greater than or equal to about 70° C. for a time period ranging from about 1 hour to about 24 hours to convert all of said formic acetic anhydride to acetic acid and gaseous carbon monoxide and to fully deplete either said acetic anhydride or said formic acid, whichever is initially present in a stoichiometric lesser amount and thereby produce a mixture comprising acetic acid and either acetic anhydride or formic acid, whichever has not been depleted; and (b) separating said acetic acid from the remainder of said mixture produced in step (a).

Specific embodiments are directed to mother liquors used in the formation of N-formylaspartic anhydride. To produce the acetic acid in accordance with this embodiment, the N-formylaspartic anhydride crystals are separated from the mother liquor, typically by filtration, and the mother liquor is processed as set forth above. The mother liquor will typically also include high boiling aspartic acid derived components. These components are easily separated from the acetic acid by simple distillation.

Once isolated, the acetic acid can be used for any number of chemical uses, including the production of aspartame.

Accordingly, it is an object of the present invention to provide a simplified process for recovering acetic acid from a mother liquor including numerous components.

It is a further object of the present invention to provide a process for recovering acetic acid from a reaction medium used to form N-formylaspartic anhydride.

These, and other objects will be readily understood by those skilled in the art as reference is made to the detailed description of the preferred embodiment.

DETAILED DESCRIPTION OF THE PREFERRED EMBODIMENT

When describing the preferred embodiment, certain terminology will be used for the sake of clarity. The use of such terminology is intended to encompass all technical equivalents which operate in a similar manner for a similar purpose to achieve a similar result.

The present invention provides a simplified process for recovering essentially pure acetic acid from a mother liquor including acetic acid, acetic anhydride, formic acid and formic acetic anhydride. In particular, the process of the present invention is used for recovering acetic acid from the mother liquor used as a reaction medium for the formation of N-formylaspartic anhydride.

As discussed above, the production of N-formylaspartic anhydride is well known in the art and is exemplified by U.S. Pat. Nos. 3,933,871; 4,526,985; 4,550,180; and 4,810,816. To the extent necessary, these patents are incorporated by reference.

The mother liquor used in the production of N-formylaspartic anhydride includes a predominant amount of acetic acid, along with minor amounts of acetic anhydride, formic acid and formic acetic anhydride. These aforementioned components are referred to as "low boiling components". The liquor will typically also include a minor amount of components derived from aspartic acid, i.e. N-formylaspartic anhydride, dipeptides derived from aspartic acid, etc. These components are referred to as "high boiling components".

With respect to the low boiling components, they are present in the equilibrium relationship shown in Equation 1.

$$HCOOH + CH_3COOCOCH_3 \rightleftharpoons CH_3COOH + HCOOCOCH_3 \quad (1)$$
(formic acid) (acetic anhydride) (acetic acid) (formic acetic anhydride)

The inventor has discovered that the formic acetic anhydride component is not heat stable and when heated to at or above 70° C., the component degrades to acetic acid and carbon monoxide. This relationship is shown in Equation 2.

$$HCOOCOCH_3 \xrightarrow{\Delta} CH_3COOH + CO(g) \quad (2)$$

By taking advantage of the equilibrium relationship of Equation 1 and the degradation reaction of Equation 2, a simplified process for isolating acetic acid is developed. First, by heating the mother liquor to above 70° C. the formic acetic anhydride becomes unstable and degrades to acetic acid and gaseous carbon monoxide, which dissolves into solution. Preferred heating conditions range from a temperature between about 70° C. and about 140° C. for a time period between about 1 hour and about 24 hours, and still more particularly, between about 2 hours and about 10 hours.

Because of the heat instability of the formic acetic anhydride, it is depleted from the mother liquor. As a result, the equilibrium relationship of Equation 1 is shifted to the right, and formic acid and acetic anhydride will combine to form formic acetic anhydride.

This mechanism is cyclic in that the depletion of formic acetic anhydride leads to the depletion of formic acid and acetic anhydride which, in turn, leads to the depletion of formic acetic anhydride. This mechanism automatically continues until all of the formic acid or acetic anhydride, whichever is present in a stoichiometric lesser amount, is depleted, and all of the formic acetic anhydride is depleted. The resulting low boiling components will include acetic acid and either acetic anhydride or formic acid, whichever is initially present in a stoichiometric excess.

To isolate the acetic acid from either the acetic anhydride or formic acid, a simple two component distillation is used. Thus, the present invention is capable of isolating acetic acid from a mother liquor initially containing four components by ultimately utilizing a simple two component distillation. Alternatively, other separation techniques such as thermal decomposition techniques may be used.

If the mother liquor initially contains high boiling components, they are easily separated from the low boiling components, typically by a simple distillation. This distillation may be performed either before or concurrently with initially heating the mother liquor, or may be performed after the acetic acid-acetic anhydride/formic acid distillation. In the preferred embodiment, this distillation takes place under a vacuum and occurs prior to the separation of the light boiling components, which are separated as described above.

For some purposes, it may be desirable to modify the mother liquor to guarantee a final acetic acid/acetic anhydride or acetic acid/formic acid mixture. All that is necessary is that additional acetic anhydride or formic acid, respectively, be added to the mother liquor such that the stoichiometric amount of the added component (including amount initially present in the mother liquor) exceeds the stoichiometric amount of the non-added component initially present.

Once the acetic acid has been separated from the mother liquor, it can be used in a number of different ways. A particularly preferred use is to utilize the pure recovered acetic acid in the production of aspartame.

The invention is further illustrated by the following non-limiting examples.

EXAMPLE 1

To produce N-formylaspartic anhydride, a solution of 32.2 g of 97% formic acid was treated with 0.2 g of MgO with stirring, followed by 115.5 g of acetic anhydride. After stirring an additional 20 minutes, 66.6 g of L-Asp were added, and the slurry was stirred at 50° C. for 5 hours. The mixture was chilled to 18° C., filtered, and the cake was washed with 50 ml of acetic acid. The mother liquor obtained was used for the acetic acid recovery and was analyzed by gas chromatography. The weight fractions of the components of the mother liquor are set forth in the Table below. The mother liquor was heated to 90° C. for 2.5 hours and another sample was taken. The procedure was repeated 2.5 hours later. Results are set forth below.

| Sample | Formic Acid | Formic Acetic Anhydride | Acetic Anhydride | Acetic Acid |
|---|---|---|---|---|
| 0 hours | 5.3 | 2.7 | 2.1 | 85.1 |
| 2.5 h/90° C. | 4.3 | 0.6 | 0.4 | 88.5 |
| 5 h/90° C. | 4.3 | <0.2 | <0.2 | 90.6 |

(The balance of the mother liquor comprised high boiling components)

This Example demonstrates that upon heating the mother liquor two components of the mixture are depleted, namely formic acetic anhydride, and acetic anhydride, which initially was present in a stoichiometric lesser amount than the stoichiometric amount of formic acid (stoichiometric ratio of formic acid to acetic anhydride was 5.75:1). Once all of the acetic anhydride and formic acetic anhydride would be depleted by additional heating, the acetic acid could easily be separated from the remaining formic acid by a simple two component distillation.

EXAMPLE 2

A synthetic mother liquor was prepared by mixing 100 ml of acetic acid, 1.2 g of acetic anhydride, and 5.0 g of formic acid. This solution was heated at 110° C. for 22 hours. Analysis of the heated sample indicated that <0.2% of formic acid, acetic anhydride and formic acetic anhydride were present in the sample. Acetic acid analysis indicated an assay of 99.3%.

EXAMPLE 3

A mother liquor sample was prepared according to the procedure of Example 1. The mother liquor was initially distilled under reduced pressure (Temp<50° C.) to separate the high boiling components from the low boiling components. The low boiling components were then heated at 114° C. for 2 hours and at 120° C. for 2 hours. This material was then fractionally distilled to remove formic acid/acetic acid as the overhead fraction and pure acetic acid as the bottom fraction. The acetic acid of the bottom fraction assayed at 99.6% with acetic anhydride, formic acid and formic acetic anhydride not being detected. The yield of recovered purified acetic acid was 86%.

Having described the invention in detail and by reference to the preferred embodiments thereof, it will be apparent modifications and variations are possible without departing from the scope of the appended claims.

What is claimed is:

1. In a process for the manufacture of N-formyl aspartic anhydride via the reaction of aspartic acid, formic acid, acetic anhydride in which crystals of N-formyl aspartic anhydride are formed and separated from a mother liquor which includes quantities of acetic acid, formic acid, acetic anhydride, formic acetic anhydride and high boiling aspartic acid derived components, the improvement comprising:

(a) separating said high boiling aspartic acid derived components from said mother liquor;
   (b) heating said mother liquor to a temperature greater than or equal to about 70° C. for a time period ranging from about 1 hour to about 24 hours to convert all of said formic acetic anhydride to acetic acid and gaseous carbon monoxide and to fully deplete either said acetic anhydride or said formic acid, whichever is initially present in a stoichiometric lesser amount and thereby produce a mixture comprising acetic acid and either acetic anhydride or formic acid, whichever has not been depleted; and
   (c) separating acetic acid initially present in the mother liquor and acetic acid formed in step (b) from the remainder of said mixture produced in step (b).

2. The process according to claim 1 wherein said step (c) comprises a simple two component distillation.

3. The process according to claim 1 wherein said heating step of step (b) comprises heating said mother liquor to a temperature between about 70° C. and about 140° C.

4. The process according to claim 3 wherein said heating step takes place for between about 2 hours to about 10 hours.

5. The process according to claim 1 comprising the additional step of adding formic acid to said mother liquid prior to step (b) such that it is present in a stoichiometric excess as compared to said acetic anhydride whereby said mixture produced in step (b) comprises formic acid and acetic acid.

6. The process according to claim 1 comprising the additional step of adding acetic anhydride to said mother liquor prior to step (b) such that it is present in a stoichiometric excess as compared to said formic acid whereby said mixture produced in step (b) comprises acetic anhydride and acetic acid.

7. The process according to claim 1 wherein said separation step (a) occurs sequentially following step (c).

* * * * *